US007883842B2

(12) United States Patent
Juhl et al.

(10) Patent No.: US 7,883,842 B2
(45) Date of Patent: *Feb. 8, 2011

(54) USE OF C3A AND DERIVATIVES THEREOF AS A BIOMARKER FOR COLORECTAL ADENOMA AND/OR CARCINOMA; METHOD FOR DETECTION AND TEST SYSTEM

(75) Inventors: Hartmut Juhl, Hamburg (DE); Kerstin David, Hamburg (DE); Anne-Kristin Fentz, Hamburg (DE)

(73) Assignee: Invidumed GmbH, Hamburg (DE)

( * ) Notice: Subject to any disclaimer, the term of this patent is extended or adjusted under 35 U.S.C. 154(b) by 428 days.

This patent is subject to a terminal disclaimer.

(21) Appl. No.: 11/660,066

(22) PCT Filed: Aug. 11, 2005

(86) PCT No.: PCT/EP2005/008742
§ 371 (c)(1),
(2), (4) Date: Feb. 12, 2007

(87) PCT Pub. No.: WO2006/053592
PCT Pub. Date: May 26, 2006

(65) Prior Publication Data
US 2008/0160515 A1 Jul. 3, 2008

(30) Foreign Application Priority Data
Aug. 13, 2004 (WO) ............... PCT/EP2004/009124

(51) Int. Cl.
*C12Q 1/00* (2006.01)
*G01N 33/53* (2006.01)
*G01N 33/574* (2006.01)

(52) U.S. Cl. ......................... 435/4; 435/7.1; 435/7.23
(58) Field of Classification Search ........................ None
See application file for complete search history.

(56) References Cited

U.S. PATENT DOCUMENTS

| 4,996,298 A | * | 2/1991 | Salem et al. ................. 530/395 |
| 6,682,740 B1 | | 1/2004 | Erdei et al. |
| 2001/0023066 A1 | | 9/2001 | Kinders et al. |

FOREIGN PATENT DOCUMENTS

| DE | 197 11 111 | 3/1997 |
| DE | 102 24 534 | 5/2002 |
| JP | 11-505019 | 5/1999 |
| JP | 2008-509407 | 3/2008 |
| WO | WO96/35955 | 11/1996 |
| WO | WO 02/059621 | 8/2002 |
| WO | WO 03/00182 | 3/2003 |
| WO | WO2004/001072 | 12/2003 |
| WO | WO 2004/013609 A2 | 2/2004 |
| WO | WO2004090550 | * 10/2004 |
| WO | WO 2005/008251 | 1/2005 |
| WO | WO2006/015615 A1 | 2/2006 |
| WO | WO2006/102526 A2 | 9/2006 |

OTHER PUBLICATIONS

Zilow et al. J. Immunological methods, 121 (1989), pp. 261-268.*
Andoh et al, Clin Exp Immuno, 1998, 111:477-483.*
Roboz et al, Proc Amer Assoc Cancer Res. vol. 45, Apr. 2004 abstract #3551.*
Codina Cazador A et al, Rev Es Enfer, Apar Dig, 1989, 75:143-8, abstract.*
Colon and rectal cancer definition of National cancer institute (2009).*
Juhl et al, J of surgical concology 64:222-230 1997.*
Belderman, et al., Chemotherapy with carboplatin/docetaxel for primary and recurrent epithelial ovarian cancer, Poster Sessions, Oct. 24, 2001, 1186.
Burger, et al., The C Terminus of the Anaphylatoxin C3a . . . , The Journal of Immunology, Jul. 15, 1998, vol. 141, 553-558, No. 2, The American Association of Immunologists, USA.
Zilow, et al., Quantitation of anaphylatoxin C3a in the presence of C3 . . . , Journal of Immunological Methods, Dec. 1, 1998, pp. 261-268, vol. 121.
Andoh, et al., Detection of complement C3 and factor B gene . . . , Clin. Exp. Immunol., Oct. 14, 1997, vol. 111, pp. 477-483, 1998.
Sarbinowski, et al., Plasma concentration of procalcitonin . . . , Acta Anaesthesiologica Scandinavica, Feb. 2005, vol. 49, pp. 191-196, 2005.
Milano et al., "Serum prealbumin, retinol-binding protein, transferrin, and albumin levels in patients with large bowel cancer," *The Journal of the National Cancer Institute*, vol. 61, No. 3, pp. 687 to 691, Sep. 1978.
Masaru Fujimori, "Clinical Significance of Ratio of Serum $a_1$ Acid Glycoprotein to Prealbumin in Colorectal Cancer," *The Japanese Journal of Gastroenterological Surgery*, vol. 24, No. 9, pp. 2363-2372, 1991.

(Continued)

*Primary Examiner*—Misook Yu
*Assistant Examiner*—Lei Yao
(74) *Attorney, Agent, or Firm*—Elliot M. Olstein; Raymond J. Lillie

(57) ABSTRACT

The present invention is directed to a method for detecting colorectal adenoma and/or colorectal carcinoma comprising the steps: a) providing an isolated sample material which has been taken from an individual, b) determining the level of C3a or a derivative thereof in said isolated sample material, c) comparing the determined level of C3a or a derivative thereof with one or more reference values. The invention is further directed to a method for discriminating between colorectal adenoma and colorectal carcinoma as well as to a method for monitoring the course of colorectal adenoma and/or colorectal carcinoma and/or the treatment of colorectal adenoma and/or colorectal carcinoma. Moreover, the invention is directed to a test system and an array for use in these methods. Furthermore, the invention is directed to the use of C3a as a biomarker for a detection of colorectal adenoma and/or colorectal carcinoma in an individual. Further, the invention is directed to method for determining whether a compound is effective in the treatment colorectal adenoma and/or colorectal carcinoma.

12 Claims, 9 Drawing Sheets

OTHER PUBLICATIONS

Roboz et al., "Identification of putative colon cancer protein biomarker by mass spectrometry": http ://www.aacrmeetingabstracts.org/egi/content/abstract/2004/1/819.

Bullen et al., "Cancer Markers in Patients Receiving Chemotherapy for Colorectal Cancer: A Preliminary Report," *Med. Ped. Oncol.* 3: 289-300 (1977).

Yuceyar et al., "The Role of Acute-Phase Reactant Proteins, Carcinoembryonic Antigen and CA 19-9 as a Marker in the Preoperative Staging of Colorectal Cancer: A Prospective Clinical Study," *Int. Surg.* 81: 136-139 (1996).

Basu, et al., J. Clinical Biochemistry and Nutrition, vol. 10, No. 1, pp. 65-70 (1991).

Gu, et al., Science in China, vol. 34, No. 11, pp. 1312-1318 (Nov. 1991).

Zhen, et al., Proceedings of the American Association for Cancer Research, vol. 45, p. 1303 (Mar. 2004).

Official Action dated Oct. 26, 2009; in Japanese Patent Application No. 2007-525256.

Pasche, et al., Best Practice of Research Clinical Gastroenterology, vol.-16, No. 2, pp. 331-345(2002).

Swahn, et al., Complement Activation in Ovarian Cancer, Poster Sessions, Abstract 1187, Oct. 24, 2001.

* cited by examiner

Figure 1

C3 (SEQ ID No.1)

C3 Protein Molekulargewicht: 185,000 Da

```
ID    CO3_HUMAN_2;  parent: CO3_HUMAN
FT    CHAIN      23     1663         Complement C3.
SQ    Sequence  1641 AA;
      SPMYSIITPN ILRLESEETM VLEAHDAQGD VPVTVTVHDF PGKKLVLSSE KTVLTPATNH
      MGNVTFTIPA NREFKSEKGR NKFVTVQATF GTQVVEKVVL VSLQSGYLFI QTDKTIYTPG
      STVLYRIFTV NHKLLPVGRT VMVNIENPEG IPVKQDSLSS QNQLGVLPLS WDIPELVNMG
      QWKIRAYYEN SPQQVFSTEF EVKEYVLPSF EVIVEPTEKF YYIYNEKGLE VTITARFLYG
      KKVEGTAFVI FGIQDGEQRI SLPESLKRIP IEDGSGEVVL SRKVLLDGVQ NLRAEDLVGK
      SLYVSATVIL HSGSDMVQAE RSGIPIVTSP YQIHFTKTPK YFKPGMPFDL MVFVTNPDGS
      PAYRVPVAVQ GEDTVQSLTQ GDGVAKLSIN THPSQKPLSI TVRTKKQELS EAEQATRTMQ
      ALPYSTVGNS NNYLHLSVLR TELRPGETLN VNFLLRMDRA HEAKIRYYTY LIMNKGRLLK
      AGRQVREPGQ DLVVLPLSIT TDFIPSFRLV AYYTLIGASG QREVVADSVW VDVKDSCVGS
      LVVKSGQSED RQPVPGQQMT LKIEGDHGAR VVLVAVDKGV FVLNKKNKLT QSKIWDVVEK
      ADIGCTPGSG KDYAGVFSDA GLTFTSSSGQ QTAQRAELQC PQPAARRRRS VQLTEKRMDK
      VGKYPKELRK CCEDGMRENP MRFSCQRRTR FISLGEACKK VFLDCCNYIT ELRRQHARAS
      HLGLARSNLD EDIIAEENIV SRSEFPESWL WNVEDLKEPP KNGISTKLMN IFLKDSITTW
      EILAVSMSDK KGICVADPFE VTVMQDFFID LRLPYSVVRN EQVEIRAVLY NYRQNQELKV
      RVELLHNPAF CSLATTKRRH QQTVTIPPKS SLSVPYVIVP LKTGLQEVEV KAAVYHHFIS
      DGVRKSLKVV PEGIRMNKTV AVRTLDPERL GREGVQKEDI PPADLSDQVP DTESETRILL
      QGTPVAQMTE DAVDAERLKH LIVTPSGCGE QNMIGMTPTV IAVHYLDETE QWEKFGLEKR
      QGALELIKKG YTQQLAFRQP SSAFAAFVKR APSTWLTAYV VKVFSLAVNL IAIDSQVLCG
      AVKWLILEKQ KPDGVFQEDA PVIHQEMIGG LRNNNEKDMA LTAFVLISLQ EAKDICEEQV
      NSLPGSITKA GDFLEANYMN LQRSYTVAIA GYALAQMGRL KGPLLNKFLT TAKDKNRWED
      PGKQLYNVEA TSYALLALLQ LKDFDFVPPV VRWLNEQRYY GGGYGSTQAT FMVFQALAQY
      QKDAPDHQEL NLDVSLQLPS RSSKITHRIH WESASLLRSE ETKENEGFTV TAEGKGQGTL
      SVVTMYHAKA KDQLTCNKFD LKVTIKPAPE TEKRPQDAKN TMILEICTRY RGDQDATMSI
      LDISMMTGFA PDTDDLKQLA NGVDRYISKY ELDKAFSDRN TLIIYLDKVS HSEDDCLAFK
      VHQYFNVELI QPGAVKVYAY YNLEESCTRF YHPEKEDGKL NKLCRDELCR CAEENCFIQK
      SDDKVTLEER LDKACEPGVD YVYKTRLVKV QLSNDFDEYI MAIEQTIKSG SDEVQVGQQR
      TFISPIKCRE ALKLEEKKHY LMWGLSSDFW GEKPNLSYII GKDTWVEHWP EEDECQDEEN
      QKQCQDLGAF TESMVVFGCP N
```

Figure 2A

C3A: 77 Aminosäuren, 9,094 Da , pI 9.7 (SEQ ID No.2)

ID   CO3_HUMAN_5;  parent: CO3_HUMAN
FT   PEPTIDE     672   748     C3a anaphylatoxin.
SQ   Sequence   77 AA;
SVQLTEKRMD KVGKYPKELR KCCEDGMREN PMRFSCQRRT RFISLGEACK
KVFLDCCNYITELRRQHARA SHLGLAR

Figure 2B

C3A-desArg: 76 Aminosäuren, pI 9,54 (SEQ ID No.3)

SVQLTEKRMD KVGKYPKELR KCCEDGMREN PMRFSCQRRT RFISLGEACK
KVFLDCCNYITELRRQHARA SHLGLA

Analysis of C3a-desArg by A) ELISA and B) SELDI-TOF MS

C3A:

ng/ml C3a-desArg

MG 8,960:

Analysis of transthyretin by A) radial immunodiffusion and B) SELDI-TOF MS

Transthyretin :

[g/l] Transthyretin

MG 13,776:

Intensity

SEQUENCE LISTING

```
<160> NUMBER OF SEQ ID NOS: 3

<210> SEQ ID NO 1
<211> LENGTH: 1641
<212> TYPE: PRT
<213> ORGANISM: human

<400> SEQUENCE: 1

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205
```

-continued

```
Ser Phe Glu Val Ile Val Glu Pro Thr Glu Lys Phe Tyr Tyr Ile Tyr
210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
                260                 265                 270

Asp Gly Ser Gly Glu Val Val Leu Ser Arg Lys Val Leu Leu Asp Gly
                275                 280                 285

Val Gln Asn Leu Arg Ala Glu Asp Leu Val Gly Lys Ser Leu Tyr Val
290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
                340                 345                 350

Phe Val Thr Asn Pro Asp Gly Ser Pro Ala Tyr Arg Val Pro Val Ala
                355                 360                 365

Val Gln Gly Glu Asp Thr Val Gln Ser Leu Thr Gln Gly Asp Gly Val
370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
                420                 425                 430

Tyr Leu His Leu Ser Val Leu Arg Thr Glu Leu Arg Pro Gly Glu Thr
                435                 440                 445

Leu Asn Val Asn Phe Leu Leu Arg Met Asp Arg Ala His Glu Ala Lys
450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
                500                 505                 510

Tyr Thr Leu Ile Gly Ala Ser Gly Gln Arg Glu Val Val Ala Asp Ser
                515                 520                 525

Val Trp Val Asp Val Lys Asp Ser Cys Val Gly Ser Leu Val Val Lys
530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
                580                 585                 590

Lys Ile Trp Asp Val Val Glu Lys Ala Asp Ile Gly Cys Thr Pro Gly
                595                 600                 605

Ser Gly Lys Asp Tyr Ala Gly Val Phe Ser Asp Ala Gly Leu Thr Phe
                610                 615                 620

Thr Ser Ser Ser Gly Gln Gln Thr Ala Gln Arg Ala Glu Leu Gln Cys
```

-continued

```
            625                 630                 635                 640
Pro Gln Pro Ala Ala Arg Arg Arg Ser Val Gln Leu Thr Glu Lys
                645                 650                 655

Arg Met Asp Lys Val Gly Lys Tyr Pro Lys Glu Leu Arg Lys Cys Cys
                660                 665                 670

Glu Asp Gly Met Arg Glu Asn Pro Met Arg Phe Ser Cys Gln Arg Arg
                675                 680                 685

Thr Arg Phe Ile Ser Leu Gly Glu Ala Cys Lys Lys Val Phe Leu Asp
            690                 695                 700

Cys Cys Asn Tyr Ile Thr Glu Leu Arg Arg Gln His Ala Arg Ala Ser
705                 710                 715                 720

His Leu Gly Leu Ala Arg Ser Asn Leu Asp Glu Asp Ile Ile Ala Glu
                725                 730                 735

Glu Asn Ile Val Ser Arg Ser Glu Phe Pro Glu Ser Trp Leu Trp Asn
                740                 745                 750

Val Glu Asp Leu Lys Glu Pro Pro Lys Asn Gly Ile Ser Thr Lys Leu
                755                 760                 765

Met Asn Ile Phe Leu Lys Asp Ser Ile Thr Thr Trp Glu Ile Leu Ala
                770                 775                 780

Val Ser Met Ser Asp Lys Lys Gly Ile Cys Val Ala Asp Pro Phe Glu
785                 790                 795                 800

Val Thr Val Met Gln Asp Phe Phe Ile Asp Leu Arg Leu Pro Tyr Ser
                805                 810                 815

Val Val Arg Asn Glu Gln Val Glu Ile Arg Ala Val Leu Tyr Asn Tyr
                820                 825                 830

Arg Gln Asn Gln Glu Leu Lys Val Arg Val Glu Leu Leu His Asn Pro
                835                 840                 845

Ala Phe Cys Ser Leu Ala Thr Thr Lys Arg Arg His Gln Gln Thr Val
                850                 855                 860

Thr Ile Pro Pro Lys Ser Ser Leu Ser Val Pro Tyr Val Ile Val Pro
865                 870                 875                 880

Leu Lys Thr Gly Leu Gln Glu Val Glu Val Lys Ala Ala Val Tyr His
                885                 890                 895

His Phe Ile Ser Asp Gly Val Arg Lys Ser Leu Lys Val Val Pro Glu
                900                 905                 910

Gly Ile Arg Met Asn Lys Thr Val Ala Val Arg Thr Leu Asp Pro Glu
                915                 920                 925

Arg Leu Gly Arg Glu Gly Val Gln Lys Glu Asp Ile Pro Pro Ala Asp
                930                 935                 940

Leu Ser Asp Gln Val Pro Asp Thr Glu Ser Glu Thr Arg Ile Leu Leu
945                 950                 955                 960

Gln Gly Thr Pro Val Ala Gln Met Thr Glu Asp Ala Val Asp Ala Glu
                965                 970                 975

Arg Leu Lys His Leu Ile Val Thr Pro Ser Gly Cys Gly Glu Gln Asn
                980                 985                 990

Met Ile Gly Met Thr Pro Thr Val Ile Ala Val His Tyr Leu Asp Glu
                995                 1000                1005

Thr Glu Gln Trp Glu Lys Phe Gly Leu Glu Lys Arg Gln Gly Ala
                1010                1015                1020

Leu Glu Leu Ile Lys Lys Gly Tyr Thr Gln Gln Leu Ala Phe Arg
                1025                1030                1035

Gln Pro Ser Ser Ala Phe Ala Ala Phe Val Lys Arg Ala Pro Ser
                1040                1045                1050
```

```
Thr Trp Leu Thr Ala Tyr Val Val Lys Val Phe Ser Leu Ala Val
1055                1060                1065

Asn Leu Ile Ala Ile Asp Ser Gln Val Leu Cys Gly Ala Val Lys
1070                1075                1080

Trp Leu Ile Leu Glu Lys Gln Lys Pro Asp Gly Val Phe Gln Glu
1085                1090                1095

Asp Ala Pro Val Ile His Gln Glu Met Ile Gly Gly Leu Arg Asn
1100                1105                1110

Asn Asn Glu Lys Asp Met Ala Leu Thr Ala Phe Val Leu Ile Ser
1115                1120                1125

Leu Gln Glu Ala Lys Asp Ile Cys Glu Glu Gln Val Asn Ser Leu
1130                1135                1140

Pro Gly Ser Ile Thr Lys Ala Gly Asp Phe Leu Glu Ala Asn Tyr
1145                1150                1155

Met Asn Leu Gln Arg Ser Tyr Thr Val Ala Ile Ala Gly Tyr Ala
1160                1165                1170

Leu Ala Gln Met Gly Arg Leu Lys Gly Pro Leu Leu Asn Lys Phe
1175                1180                1185

Leu Thr Thr Ala Lys Asp Lys Asn Arg Trp Glu Asp Pro Gly Lys
1190                1195                1200

Gln Leu Tyr Asn Val Glu Ala Thr Ser Tyr Ala Leu Leu Ala Leu
1205                1210                1215

Leu Gln Leu Lys Asp Phe Asp Phe Val Pro Pro Val Val Arg Trp
1220                1225                1230

Leu Asn Glu Gln Arg Tyr Tyr Gly Gly Gly Tyr Gly Ser Thr Gln
1235                1240                1245

Ala Thr Phe Met Val Phe Gln Ala Leu Ala Gln Tyr Gln Lys Asp
1250                1255                1260

Ala Pro Asp His Gln Glu Leu Asn Leu Asp Val Ser Leu Gln Leu
1265                1270                1275

Pro Ser Arg Ser Ser Lys Ile Thr His Arg Ile His Trp Glu Ser
1280                1285                1290

Ala Ser Leu Leu Arg Ser Glu Glu Thr Lys Glu Asn Glu Gly Phe
1295                1300                1305

Thr Val Thr Ala Glu Gly Lys Gly Gln Gly Thr Leu Ser Val Val
1310                1315                1320

Thr Met Tyr His Ala Lys Ala Lys Asp Gln Leu Thr Cys Asn Lys
1325                1330                1335

Phe Asp Leu Lys Val Thr Ile Lys Pro Ala Pro Glu Thr Glu Lys
1340                1345                1350

Arg Pro Gln Asp Ala Lys Asn Thr Met Ile Leu Glu Ile Cys Thr
1355                1360                1365

Arg Tyr Arg Gly Asp Gln Asp Ala Thr Met Ser Ile Leu Asp Ile
1370                1375                1380

Ser Met Met Thr Gly Phe Ala Pro Asp Thr Asp Asp Leu Lys Gln
1385                1390                1395

Leu Ala Asn Gly Val Asp Arg Tyr Ile Ser Lys Tyr Glu Leu Asp
1400                1405                1410

Lys Ala Phe Ser Asp Arg Asn Thr Leu Ile Ile Tyr Leu Asp Lys
1415                1420                1425

Val Ser His Ser Glu Asp Asp Cys Leu Ala Phe Lys Val His Gln
1430                1435                1440
```

```
Tyr Phe Asn Val Glu Leu Ile Gln Pro Gly Ala Val Lys Val Tyr
1445                1450                1455

Ala Tyr Tyr Asn Leu Glu Glu Ser Cys Thr Arg Phe Tyr His Pro
1460                1465                1470

Glu Lys Glu Asp Gly Lys Leu Asn Lys Leu Cys Arg Asp Glu Leu
1475                1480                1485

Cys Arg Cys Ala Glu Glu Asn Cys Phe Ile Gln Lys Ser Asp Asp
1490                1495                1500

Lys Val Thr Leu Glu Glu Arg Leu Asp Lys Ala Cys Glu Pro Gly
1505                1510                1515

Val Asp Tyr Val Tyr Lys Thr Arg Leu Val Lys Val Gln Leu Ser
1520                1525                1530

Asn Asp Phe Asp Glu Tyr Ile Met Ala Ile Glu Gln Thr Ile Lys
1535                1540                1545

Ser Gly Ser Asp Glu Val Gln Val Gly Gln Gln Arg Thr Phe Ile
1550                1555                1560

Ser Pro Ile Lys Cys Arg Glu Ala Leu Lys Leu Glu Glu Lys Lys
1565                1570                1575

His Tyr Leu Met Trp Gly Leu Ser Ser Asp Phe Trp Gly Glu Lys
1580                1585                1590

Pro Asn Leu Ser Tyr Ile Ile Gly Lys Asp Thr Trp Val Glu His
1595                1600                1605

Trp Pro Glu Glu Asp Glu Cys Gln Asp Glu Glu Asn Gln Lys Gln
1610                1615                1620

Cys Gln Asp Leu Gly Ala Phe Thr Glu Ser Met Val Val Phe Gly
1625                1630                1635

Cys Pro Asn
1640

<210> SEQ ID NO 2
<211> LENGTH: 77
<212> TYPE: PRT
<213> ORGANISM: human

<400> SEQUENCE: 2

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
                20                  25                  30

Arg Phe Ser Cys Gln Arg Arg Thr Arg Phe Ile Ser Leu Gly Glu Ala
            35                  40                  45

Cys Lys Lys Val Phe Leu Asp Cys Cys Asn Tyr Ile Thr Glu Leu Arg
        50                  55                  60

Arg Gln His Ala Arg Ala Ser His Leu Gly Leu Ala Arg
65                  70                  75

<210> SEQ ID NO 3
<211> LENGTH: 76
<212> TYPE: PRT
<213> ORGANISM: human

<400> SEQUENCE: 3

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
                20                  25                  30
```

```
                                -continued
Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
        50                  55                  60

Arg Gln His Ala Arg Ala Ser His Leu Gly Leu Ala
65                  70                  75
```

USE OF C3A AND DERIVATIVES THEREOF AS A BIOMARKER FOR COLORECTAL ADENOMA AND/OR CARCINOMA; METHOD FOR DETECTION AND TEST SYSTEM

The present invention relates to the field of detection of colorectal adenoma and/or colorectal carcinoma.

Colorectal carcinoma is the third most frequently diagnosed carcinoma (9.4%) worldwide. In 2003 nearly 945 000 new cases of colorectal carcinoma were diagnosed worldwide and approximately 492 000 people died of this disease. The incidence of colorectal carcinoma is increasing, while the mortality rate of colorectal carcinoma is decreasing. Incidence of colorectal carcinoma increases with age, beginning at around 40 years of age, and it is higher for men than for women (40.6 for men versus 30.6 for women, per 100 000 per year) (World cancer report, 2003, Ed. B W. Stewart and P. Kleihues. IARC Press, Lyon).

In most patients, development of colorectal carcinoma follows a multistep progression from premalignant adenoma to invasive malignancies that have the propensity for metastasis. There is evidence that reduction in colorectal carcinoma morbidity and mortality can be achieved through detection and treatment of early-stage colorectal carcinomas and identification and removal of colorectal adenomatous polyps, which are precursors of colorectal carcinoma.

So far only invasive colorectal screening tests such as colonoscopy have been shown to achieve detection of early stage colorectal carcinoma and its precursors, i.e. adenomatous polyps and/or flat neoplastic areas. Several tests are available as options for colorectal carcinoma screening. The screening tests encompass faecal occult blood testing (FOBT), flexible sigmoidoscopy, FOBT combined with flexible sigmoidoscopy and colonoscopy. The various screening tests differ from each other regarding performance, effectiveness, possible screening frequency, test complications, costs and acceptance by patients.

Screening by the faecal occult blood test is currently considered to be the optimal screening strategy in terms of cost-effectiveness. Occult blood in stool can be detected by chemical agents such as guaiac, through hemeporphyrin or immunological methods. The guaiac slide test Hemoccult (II) available from SmithKline Diagnostics is most widely used.

Various technical factors affect its clinical performance. Hemoccult has about 50% sensitivity for colorectal carcinomas and about 98% specificity, however, the sensitivity is low for polyps, at around 10% (Simon J B. (1998) Gastroenterologist 6:66-78. Review). Another important drawback of occult blood screening is the poor accuracy of prediction, only 10% of positive reactions prove to be due to colorectal carcinoma (Simon J B. (1998) Gastroenterologist 6:66-78. Review; Mandel J S et al. (1999) J. Natl. Cancer Inst. 91:434-437; Hardcastle J D et al. (1996) Lancet 348:1472-1477; Kronborg O et al. (1996) Lancet 348:1467-71; Winawer S J et al. (1997) Gastroenterology 112:594-642; Fletcher R H (1998) N. Engl. J. Med. 338:1153-1154).

Moreover, a faecal occult blood test does only provide results after progression of the disease to a certain stage. It would be desirable to have a test system allowing the detection of colorectal adenoma and/or colorectal carcinoma at an earlier point in time.

More recently developed immunological tests generally have high sensitivity, however, a poor specificity which remains an important problem. Other methods, such as genetic testings of stool samples for KRAS oncogenes and for p53 protein, are not yet cost-effective and have a low sensitivity (Calistri D et al. (2003) Clin. Gastroenterol. Hepatol. 1:377-383; Schoen R E (2002) Nat. Rev. Cancer 2:65-70).

Endoscopy (Kavanagh A M (1998) Cancer Causes Control 9:455-462), using either the flexible sigmoidoscope or the colonoscope (Lieberman D A (1997) Gastroenterol. Clin. N. Am. 26: 71-83), is the most definitive means of detection, but has limitations.

The false negative rate for flat neoplastic lesions has been recognized and remains to be high (Kudo S (1997) Gastrointest. Endosc. Clin. N. Am. 7:87-98.). Colonoscopy permits examination of the colon with a low false negative rate for polypoid lesions of at least 10 mm in diameter. For this reason, the intervals allowed before re-examination are relatively long after a negative assessment (up to ten years) or up to five years after polypectomy.

However, patient compliance with such recommendation for reexamination after colonoscopy is poor. Moreover, a colonoscopy is costly and cumbersome. In view of the high costs of a generalized examination and the limited acceptance of a colonoscopy by the population this examination method has a limited application.

Isolated tissue samples, which are collected, can be tested for colorectal carcinoma and its precursor, colorectal adenoma, by various methods. DE 197 11 111A discloses a method using an in vitro determination of intraepithelial colon bacteria, components and reaction products thereof. Another method using HERG gene expression in tissue samples is disclosed in DE 102 24 534.

CEA-(Carcinoembryonic antigen)-levels in blood samples have been used to detect colon carcinoma. However, CEA levels are not specifically elevated in colon carcinoma and have been shown to be elevated also in patients with other malignant diseases (e.g., cancers of the stomach, pancreas, breast, and lung) and with various nonmalignant conditions (e.g., alcoholic liver disease, inflammatory bowel disease, heavy cigarette smoking, chronic bronchitis, and pancreatitis). (Posner M R, Mayer R J: The use of serologic tumor markers in gastro intestinal malignancies. Hematol Oncol Clin North Am 8:533, 1994). Further, the CEA-levels are not elevated in colon adenomas.

An object of the invention is to provide means allowing an early detection of colon adenoma and/or colon carcinoma.

It is a further object to provide means of allowing an selective and specific detection of colon adenoma and/or colon carcinoma by a non-invasive method.

It is a further object to provide a biomarker which can be used in the detection of colorectal adenoma and/or carcinoma.

Another object of the present invention is to provide a test system for detecting colorectal adenoma or carcinoma which is cost effective and can be widely used.

Moreover, the test system should be easy to handle and more convenient for the individual to be examined for colorectal adenoma and/or carcinoma.

It is a further object of the present invention to provide a screening system for determining whether a compound is effective in the treatment of colorectal adenoma and/or carcinoma.

The objects underlying the present invention are solved by the use of C3a or a derivative thereof as a biomarker for the detection of colorectal adenoma and/or colorectal carcinoma in an individual. The detection can be carried out in vivo and in vitro. Pursuant to a preferred embodiment, the detection is carried out in vitro.

The objects are further solved by a method for detecting colorectal adenoma and/or colorectal carcinoma comprising the steps:

a) providing an isolated sample material which has been taken from an individual,
b) determining the level of C3a or a derivative thereof in said isolated sample material,
c) comparing the determined level of C3a or a derivative thereof with one or more reference values.

The objects are further solved by a method for discriminating between colorectal adenoma and colorectal carcinoma comprising the steps:
a) providing an isolated sample material which has been taken from an individual,
b) determining the level of C3a or a derivative thereof in said isolated sample material,
c) comparing the determined level of C3a or a derivative thereof with one or more reference values.

The objects are also solved by a method for monitoring the development and/or the course and/or the treatment of colorectal adenoma and/or colorectal carcinoma comprising the steps:
a) providing an isolated sample material which has been taken from an individual,
b) determining the level of C3a or a derivative thereof in said isolated sample material,
c) comparing the determined level of C3a or derivative thereof with one or more reference values.

In a preferred embodiment the effectiveness of a surgical or therapeutical procedure is controlled in order to decide as to whether the colorectal adenoma and/or colorectal carcinoma is completely removed. In another embodiment the therapy of an colorectal adenoma and/or colorectal cancer patient with one or more chemical substances, antibodies, antisense-RNA, radiation, e.g. X-rays or combinations thereof is controlled in order to control the effectiveness of the treatment.

The objects are solved as well by providing a test system for detecting colorectal adenoma and/or colorectal cancer in a sample of an individual comprising:
a) an antibody or a receptor which binds to an epitope of C3a or a derivative thereof,
b) a solid support which supports said antibody or receptor,
c) a reagent for detecting the binding of said epitope of C3a or a derivative thereof to said antibody or receptor.

The objects are furthermore solved by the provision of an array comprising detection molecules for detecting of colorectal adenoma and/or colorectal carcinoma in an individual comprising as detection molecule:
a) a nucleic acid probe immobilized to a solid support for binding to and detecting mRNA encoding C3a or a derivative thereof and/or for binding to and detecting C3a proteins or derivatives thereof, or
b) an antibody immobilized to a solid support for binding to and detecting of an epitope of C3a or a derivative thereof, or
c) a receptor immobilized to a solid support for binding to and detecting of an epitope of C3a or a derivative thereof, wherein preferably each different amounts of detection molecules are immobilized to the solid support to increase the accuracy of the quantification.

The nucleic acid probe is for example selected from the group consisting of single-stranded or double-stranded DNA or RNA, aptamers and combinations thereof. Aptamers are single-stranded oligonucleotides that assume a specific, sequence-dependent shape and bind to protein targets with high specificity and affinity. Aptamers are identified using the SELEX process (Tuerk C. and Gold L. (1990) Science 249: 505-510; Ellington A D and Szostak J W. (1990) Nature 346: 818-822).

The objects are furthermore solved by a method for determining whether a compound is effective in the treatment of colorectal adenoma and/or colorectal carcinoma comprising the steps:
a) treating of a colorectal adenoma or colorectal carcinoma patient with a compound,
b) determining the level of C3a or a derivative thereof in a sample material of said patient, and
c) comparing the determined level of C3a or a derivative thereof with one or more reference values.

Preferred embodiments are specified in dependent claims.

According to the present invention the term "sample material" is also designated as "sample".

Pursuant to the present invention the term "biomarker" is meant to designate a protein or protein fragment or a nucleic acid which is indicative for the incidence of the colorectal adenoma and/or colorectal carcinoma. That means the "biomarker" is used as a mean for detecting colorectal adenoma and/or colorectal carcinoma.

The term "individual" or "individuals" is meant to designate a mammal. Preferably, the mammal is a human being such as a patient.

The term "healthy individual" or "healthy individuals" is meant to designate individual(s) not diseased of colorectal adenoma and/or colorectal carcinoma. That is to say, the term "healthy individual(s)" is used only in respect of the pathological condition of colorectal adenoma and/or colorectal carcinoma and does not exclude the individual to suffer from diseases other than colorectal adenoma and/or colorectal carcinoma.

The term "derivative thereof" is meant to describe any modification on DNA, mRNA or protein level comprising e.g. the truncated gene, fragments of said gene, a mutated gene, or modified gene. The term "gene" includes nucleic acid sequences, such as DNA, RNA, mRNA or protein sequences or oligopeptide sequences or peptide sequences. The derivative can be a modification which is an result of a deletion, substitution or insertion of the gene. The gene modification can be a result of the naturally occurring gene variability. The term "naturally occurring gene variability" means modifications which are not a result of genetic engineering. The gene modification can be a result of the processing of the gene or gene product within the body and/or a degradation product. The modification on protein level can be due to enzymatic or chemical modification within the body. For example the modification can be a glycosylation or phosphorylation or farnesylation. Preferably, the derivative codes for or comprises at least 5 amino acids, more preferably 10 amino acids, most preferably 20 amino acids of the unmodified protein. In one embodiment the derivative codes for at least one epitope of the respective protein.

The term "C3a or a derivative thereof" as used in the present invention also comprises truncated C3a, fragments of C3a, mutated C3a, modified C3a or the precursor C3 (FIG. 1, SEQ ID No. 1) or fragments of C3. In one embodiment the derivative has a protein sequence identity of 80%, preferably 90%, more preferably 98% with the sequence SEQ-ID-No. 2 (FIG. 2A, SEQ ID No. 2). The modification of "C3a" can be due to enzymatic or chemical modification. In particular, the term C3a or a derivative thereof especially comprises a truncated C3a-protein preferably having a molecular weight in the range of 8,950±25 Da; more preferably in the range of 8,950±20 Da. In a preferred embodiment the truncated C3a-protein has a molecular weight of 8,939 Da. Preferably, the C3a-protein has no C-terminal Arginin and optionally a molecular weight in the range of 8,950±20 Da. In one embodiment the C3a derivative is C3a-desArg (FIG. 2B, SEQ ID No. 3). In one embodiment the C3a derivative is obtained by cleavage of C3a by mastcell-chymase. In another embodiment the C3a is obtained by cleavage of C3 by C3-convertase.

C3a belongs to the group of anaphylatoxins. C3a, C4a and C5a are proteolytic products of serine proteases of the complement system. C3a (SEQ-ID-No. 2) is derived from the third component (C3) (SEQ-ID-No. 1) of the blood complement system during complement activation. C3a is a hormon with local effectiveness. Approximately 40% of the amino acid residues in C3a are involved in a helical conformation. Serum anaphylatoxins are involved in a variety of cellular immune responses, as well as being potent proinflammatory agents. C3a produces powerful effects on blood vessel walls, contraction of smooth muscle and an increase in vascular permeability. The C-terminal arginine in C3a is of fundamental importance for its biological activity. Anaphylatoxins are regulated by carboxypeptidase N (anaphylatoxin inactivator), which removes within seconds the carboxyterminal arginine. This mechanism converts the intact anaphylatoxin into a less active C3a-desArg form (SEQ ID No. 3).

The term "epitope" is meant to designate any structural element of a protein or peptide or any proteinaceous structure allowing the specific binding of an antibody, an antibody fragment, a protein or peptide structure or a receptor.

The methods of the present invention are carried out with sample material such as a body fluid or tissue sample which already has been isolated from the human body. Subsequently the sample material can be fractionated and/or purified. It is for example possible, to store the sample material to be tested in a freezer and to carry out the methods of the present invention at an appropriate point in time after thawing the respective sample material.

It has been surprisingly discovered by the present inventors that the protein C3a or a derivative thereof can be used as a biomarker for the detection of colorectal adenoma and/or carcinoma. The inventors have now surprisingly found that the level protein C3a or a derivative thereof in a body fluid is elevated in individuals having colorectal adenoma and/or carcinoma. Furthermore, the protein C3a level or a derivative thereof in a body fluid can be used to distinguish healthy people from people having colorectal adenoma and/or carcinoma as well as people having colorectal adenoma from people having colorectal carcinoma.

Pursuant to the present invention, sample material can be tissue, cells or a body fluid. Preferably the sample material is a body fluid such as blood, blood plasma, blood serum, bone marrow, stool, synovial fluid, lymphatic fluid, cerebrospinal fluid, sputum, urine, mother milk, sperm, exudate and mixtures thereof. In a preferred embodiment the body fluids are fractionated with anion exchange chromatography. The C3a protein is for example eluted at pH 9.0. The transthyretin protein (p13,776) is for example eluted at pH 4.0.

Preferably, the body fluid has been isolated before carrying out the methods of the present invention. The methods of the invention are preferably carried out in vitro by a technician in a laboratory.

According to a preferred embodiment of the invention, C3a is measured in blood plasma or blood serum. Blood serum can be easily obtained by taking blood from an individual to be medically examined and separating the supernatant from the clotted blood.

The level of C3a or a derivative thereof in the body fluid, preferably blood serum, is higher with progressive formation of colorectal adenoma. The colorectal adenoma is a benign neoplasma which may become malign. When developing colorectal cancer from benign colorectal adenoma, the level of C3a or a derivative thereof in body fluids, preferably blood serum, further is elevated.

After transformation of colorectal adenoma into colorectal cancer, the pathological condition of the afflicted individual can be further exacerbated by formation of metastasis.

The present invention provides an early stage biomarker which allows to detect the neoplastic disease at an early and still benign stage, neoplastic disease at an early stage or benign stage and/or early tumor stages. The early detection enables the physician to timely remove the colorectal adenoma and to dramatically increase the chance of the individual to survive.

Moreover, the present invention allows to monitor the level of C3a or a derivative thereof in a body fluid such as blood serum over an extended period of time, such as years.

The long term monitoring allows to differentiate between healthy individuals and colorectal adenoma and/or colorectal carcinoma. The level of C3a or a derivative thereof can be routinely checked, for example, once or twice a year. If an increase of the level of C3a or a derivative thereof is detected this can be indicative for colorectal adenoma and/or early colorectal carcinoma. A further increase of the level of C3a or a derivative thereof can then be indicative for the transformation into malign colorectal carcinoma.

Moreover, the course of the disease and/or the treatment can be monitored. If the level of C3a or a derivative thereof further increases, for example after removal of the colorectal adenoma, this can be indicative for exacerbation of the pathological condition.

That means, the level of C3a or a derivative thereof is a valuable clinical parameter for detecting and/or monitoring of colorectal adenoma and/or colorectal carcinoma. The level of C3a or a derivative thereof in body fluids is higher after incidence of colorectal adenoma. Therefore, the level of C3a or a derivative thereof is an important clinical parameter to allow an early diagnosis and, consequently, an early treatment of the disease. In a preferred embodiment patients with elevated C3a levels or derivatives thereof are subsequently examined by colonoscopy.

The method of the invention for detection of colorectal adenoma and/or colorectal carcinoma comprises the step of providing an isolated sample material which has been taken from an individual, then determining the level of C3a or a derivative thereof in the isolated sample material, and finally comparing the determined level of C3a or a derivative thereof with one or more reference values. In one embodiment, one or more further biomarker(s) is/are additionally detected in an isolated sample material which has been taken from an individual, the level of the biomarker(s) is/are determined and compared with one or more respective reference values.

The reference value can be calculated as the average level of C3a or a derivative thereof determined in a plurality of isolated samples of healthy individuals or individuals suffering from colorectal adenoma and/or colorectal carcinoma. This reference value can be established as a range to be considered as normal meaning that the person is healthy or suffers from colorectal adenoma and/or colorectal carcinoma. A specific value within a range can then be indicative for healthy condition or the pathological condition of colorectal adenoma and/or colorectal carcinoma. This range of reference value can be established by taking a statistically relevant number of body fluid samples, such as serum samples, of healthy individuals as it is done for any other medical parameter range such as, e.g., blood sugar. Preferably, two reference values are calculated which are designated as negative control and positive control 1. The reference value of the negative control is calculated from healthy individuals and the positive control is calculated from individuals suffering from colorectal adenoma or colorectal carcinoma. More preferably, three reference values are calculated which are designated as negative control and positive control 1 and positive control 2. Positive control 1 can be calculated from individuals suffering from colorectal carcinoma and positive control 2 can be calculated from individuals suffering from colorectal adenoma.

In an another embodiment of the present invention, the reference values can be individual reference values calculated as the average level of C3a or a derivative thereof determined in a plurality of isolated samples taken from the individual over a period of time.

When monitoring the level of C3a or a derivative thereof over an extended period of time, such as months or years, it is possible to establish an individual average level. The C3a or a derivative thereof level can be measured, for example, from the same blood serum sample when measuring blood sugar and can be used to establish an individual calibration curve allowing to specifically detect any individual increase of the level of C3a or a derivative thereof.

The reference value for further biomarkers can also be calculated in the same way as described for C3a. The average levels of C3a or further biomarkers may be the mean or median level.

In another aspect the present invention further provides a test system for detecting colorectal adenoma and/or colorectal carcinoma in an isolated sample material of an individual. The test system is based either on the specificity of an antibody or a receptor to specifically bind to an epitope or a suitable structural element of C3a or a derivative thereof or a fragment of thereof. A receptor can be any structure able to bind specifically to C3a or a derivative thereof. The receptor can be, for example, an antibody fragment such as an Fab or an F(ab')$_2$ fragment or any other protein or peptide structure being able to specifically bind to C3a or a derivative thereof.

The antibody, antibody fragment or receptor is bound to a solid support such as, e.g., a plastic surface or beads to allow binding and detection of C3a or a derivative thereof. For example, a conventional microtiter plate can be used as a plastic surface. The detection of the binding of C3a or a derivative thereof can be effected, for example, by using a secondary antibody labelled with a detectable group. The detectable group can be, for example, a radioactive isotop or an enzyme like horseradish peroxidase or alkaline phosphatase detectable by adding a suitable substrate to produce, for example, a colour or a fluorescence signal.

The test system can be an immunoassay such as an enzyme-linked immunosorbentassay (ELISA) or an radio immunoassay (RIA) or luminescence immunossay (LIA). However, any other immunological test system using the specificity of antibodies or fragments of antibodies can be used such as Western blotting or immuno precipitation.

The present invention also provides an array comprising detection molecules for detecting colorectal adenoma and/or colorectal carcinoma in an individual, wherein the detection molecule can be a nucleic acid probe immobilized on a solid support for binding to and detecting of mRNA encoding C3a, fragments, mutations, variants or derivatives thereof, or an antibody immobilized on a solid support for binding to and detecting of an epitope of C3a or a derivative thereof, or a receptor immobilized on a solid support for binding to and detecting of an epitope of C3a or a derivative thereof. Preferably, the array comprises further detection molecules which are biomarkers for detecting colorectal adenoma and colorectal carcinoma.

The nucleic acid probe can be any natural occurring or synthetic oligonucleotide or chemically modified oligonucleotides, as well as cDNA, cRNA, aptamer and the like.

Alternatively, the present invention also comprises an inverse array comprising patient samples immobilized on a solid support which can be detected by the above defined detection molecules.

Preferably the array comprises detection molecules which are immobilized to a solid surface at identifiable positions.

The term "array" as used in the present invention refers to a grouping or an arrangement, without being necessarily a regular arrangement. An array comprises preferably at least 2, more preferably 5 different sets of detection molecules or patient samples. Preferably, the array of the present invention comprises at least 50 sets of detection molecules or patient samples, further preferred at least 100 sets of detection molecules or patient samples. Pursuant to another embodiment of the invention the array of the present invention comprises at least 500 sets of detection molecules or patient samples. The detection molecule can be for example a nucleic acid probe or an antibody or a receptor.

The described array can be used in a test system according to the invention. The array can be either a micro array or a macro array.

The detection molecules are immobilised to a solid surface or support or solid support surface. This array or microarray is then screened by hybridising nucleic acid probes prepared from patient samples or by contacting the array with proteinaceous probes prepared from patient samples.

The support can be a polymeric material such as nylon or plastic or an inorganic material such as silicon, for example a silicon wafer, or ceramic. Pursuant to a preferred embodiment, glass ($SiO_2$) is used as solid support material. The glass can be a glass slide or glass chip. Pursuant to another embodiment of the invention the glass substrate has an atomically flat surface.

For example, the array can be comprised of immobilized nucleic acid probes able to specifically bind to mRNA of C3a or a derivative thereof or antibodies specifically bind to C3a protein or derivatives thereof being present in a body fluid such as serum. Another preferred embodiment is to produce cDNA by reverse transcription of C3a encoding mRNA or of mRNA encoding a derivative of C3a and to specifically detect the amount of respective cDNA with said array. The array technology is known to the skilled person. A quantification of the measured mRNA or cDNA or proteins, respectively, can be effected by comparison of the measured values with a standard or calibration curve of known amounts of C3a or a derivative thereof mRNA or cDNA or proteins.

Preferably, different amounts of detection molecules are immobilized each on the solid support to allow an accurate quantification of the level of C3a or a derivative thereof.

Pursuant to another embodiment of the invention, the level of C3a or a derivative thereof is determined by mass spectroscopy.

Mass spectroscopy allows to specifically detect C3a or a derivative thereof via its molecular weight and to quantify the amount of C3a or a derivative thereof very easily.

Any suitable ionization method in the field of mass spectroscopy known in the art can be employed to ionize the C3a or a derivative thereof molecule, fragments, mutations, variants or derivatives thereof. The ionization methods comprise electron impact (EI), chemical ionization (CI), field ionization (FDI), electrospray ionization (ESI), laser desorption ionization (LDI), matrix assisted laser desorption ionization (MALDI) and surface enhanced laser desorption ionization (SELDI).

Any suitable detection method in the field of mass spectroscopy known in the art can be employed to determine the molecular mass of C3a or a derivative thereof. The detection methods comprise quadrupol mass spectroscopy (QMS), fourier transform mass spectroscopy (FT-MS) and time-of-flight mass spectroscopy (TOF-MS).

Preferably, the mass spectroscopy is a surface enhanced laser desorption ionization-time of flight-mass spectroscopy (SELDI-TOF-MS). Before carrying out a SELDI-TOF-MS, the C3a or a derivative thereof in the isolated sample is preferably immobilized on a chip or solid support with an activated surface. The activated surface comprises preferably immobilized antibodies against anti-C3a or a derivative thereof such as, for example, rabbit polyclonal-antibodies. After binding of the C3a or a derivative thereof to the antibodies, a time-of-flight analysis in a SELDI-TOF mass spectrometer is carried out, which delivers intensity signals for determination of the C3a or a derivative thereof level.

Moreover, mass spectroscopy allows to simultaneously detect other proteins which can have a relevance with respect to the detection of colorectal adenoma and/or colorectal cancer.

In an embodiment of the present invention the sensitivity and/or specificity of the detection of colorectal adenoma and/or colorectal carcinoma is enhanced by additionally detection of a further biomarker. In particular, in one embodiment the sensitivity and/or specificity of the detection of colorectal adenoma and/or colorectal carcinoma is enhanced by detection of another protein or nucleic acid in combination with C3a or a derivative thereof.

Preferably, the sensitivity and specificity of the methods, arrays, test systems and uses according to the present invention are increased by the combination of detecting C3a and derivatives thereof with transthyretin and derivatives thereof.

The term "transthyretin or a derivative thereof" as used in the present invention also comprises truncated transthyretin, fragments of transthyretin, mutated transthyretin, or modified transthyretin. The modification of "transthyretin" can be due to enzymatic or chemical modification. Moreover, the term "transthyretin" is also used to designate monomeric or multimeric forms of transthyretin. For example, the term "transthyretin" especially covers the monomeric protein chain usually being part of the homotetrameric protein transthyretin.

Transthyretin is also designated as prealbumin. Transthyretin is a tetrameric protein having a molecular weight of about 54,000 Da that is synthesized mainly in the liver Transthyretin is normally a homotetramer comprising four protein chains having each a molecular weight of about 14,000 Da. Using mass spectroscopy the inventors have detected several variants of the transthyretin protein chains having a molecular weight of inter alia 13,776 Da, 13,884 Da or 14,103 Da. The inventors have found out that especially the level of molecular variants of transthyretin having a molecular weight of 13,776 Da and 13,884 Da is decreased in a body fluid such as serum in case of incidence of colorectal adenoma and/or colorectal carcinoma.

In a further embodiment of the present invention the sensitivity and/or specificity of the detection of colorectal adenoma and/or colorectal carcinoma is enhanced by additionally detection of p53, CEA (carcinoembryonic antigen) and/or CA 19-9, CA 15-3, Kras, mutated E-cadherin, β-Catenin or derivatives thereof in combination with C3a or a derivative thereof.

In a further embodiment of the present invention the sensitivity and/or specificity of the detection of colorectal adenoma and/or colorectal carcinoma can be enhanced by additionally detection of mutations in DNA mismatch genes, e.g. MSH2, MSH3, MLH1, PMS1, PMS2, MSH6, microsatellite instability of e.g. MHL1 or MSH2, SNPs (single nucleotide polymorphysm) or C-reactive protein plasma concentrations.

In a further embodiment of the present invention the sensitivity and/or specificity of the detection of colorectal adenoma and/or colorectal carcinoma is optionally enhanced by detection of CA15-3, CA-125 and/or Her-2/neu in combination with C3a or a derivative thereof. CA15-3 is an oncofetal antigen, which is expressed by several carcinomas, and is often measured with other tumor markers. Both CA15-3 and CA-125 are prognostic indicators, mainly for breast cancer, but also in addition to visceral metastases. The amplification of Her-2/neu in breast carcinoma is associated with poor prognosis, short disease-free interval and short survival time. Little is known up to now about the starting point of amplification and the progress of Her-2/neu up to now.

In a preferred embodiment colorectal adenoma and/or colorectal carcinoma are detected by the combination of the biomarkers C3a and transthyretin or derivatives thereof. This allows the detection of colorectal adenoma and/or colorectal carcinoma with an increased sensitivity and/or specificity. Further, the detection method is well accepted by the patients, since the detection method is non-invasive.

The sensitivity and specificity are defined as follow:

The sensitivity is the number of true positive patients (%) with regard to the number of all patients (100%). The patients are individuals having colorectal adenoma and/or colorectal carcinoma.

The specificity is the number of true negative individuals (%) with regard to the number of all healthy individuals (100%).

The sensitivity and specificity can be alternatively defined by the following formulas:

|  |  | diagnosis | |
|---|---|---|---|
|  |  | + | − |
| test | + | TP | FP |
|  | − | FN | TN |

TP: True positive (test positiv, diagnosis correct);
FP: False positive (test positiv, diagnosis incorrect);
TN: True negative (test negative, diagnosis correct);
FN: False negative (test negative, diagnosis incorrect);

The sensitivity is calculated by the following formula:

TP/(TP+FN)

and the specificity is calculated by the following formula:

TN/(TN+FP)

The result of each analysis group, which is selected from TP, FP, TN, FN, is calculated for a plurality of isolated samples selected from the group consisting of healthy individuals, colorectal adenoma patients and/or colorectal carcinoma patients. TP, FP, TN, FN relates to number of individuals that are correlated with the status true positive, false positive, true negative, false negative, respectively.

The methods of the present invention can be carried out in combination with other diagnostic methods for detection of colorectal adenoma and/or colorectal carcinoma to increase the overall sensitivity and/or specificity. The detection of C3a allows an very early detection of colorectal adenoma and can therefore be used as an very early marker.

Preferably, the methods of the present invention are carried out as an early detection and/or monitoring method. If the results of the methods of the present invention should indicate the incidence of colorectal adenoma and/or colorectal adenoma, further examinations such as colonoscopy should be carried out.

The following polyclonal anti-transthyretin antibodies and C3a antibodies can be used when practicing the invention:

Anti-transthyretin: PC 066 available from The Binding Site Ltd., Birmingham, England and A 0002, available from DAKO, Hamburg, Germany.

Anti-C3a-desArg: available with the Quidel immunoassay (Quidel Corporation, 10165 McKellar Court, San Diego, Calif. 92121, USA).

The present invention further provides a method for determining whether a compound is effective in the treatment colorectal adenoma and/or colorectal carcinoma.

The method for determining whether a compound is effective in the treatment colorectal adenoma and/or colorectal carcinoma comprises the steps of:

a) treating of a colorectal adenoma or colorectal carcinoma patient with a compound
b) determining the level of C3a or a derivative thereof in a sample material of said patient
c) comparing the determined level of C3a or a derivative thereof with one or more reference values.

The term "patient" as used in the present application covers humans as well as non-human beings such as animals. The animals are preferably selected from the group consisting of rodents, e.g. mouse, rat, hamster, and other animals, e.g. guinea-pig, rabbit, hare, dog and pig.

These animals can be used to specifically induce certain disease states, like colorectal adenoma and colorectal carcinoma, for research purposes. The induction of said disease states can, for example, be effected by treatment of the animals, for example, with radioactive or chemical substances known to induce colorectal cancer or colorectal adenoma disease state. The disease states can also be induced using viral transfection systems. It is also possible to use genetically modified animals, in which one or more specific gene function(s) has/have been altered, or knock-out animals such as knock-out mice in which a specific gene function has been deleted.

The "compound" can be one or more chemical substances, an antibody, protein, peptide, antisense mRNA, small molecular drug, or combinations thereof. The compound can also be replaced by irradiation, e.g. X-ray, or combinations of compounds and radiation can be used.

The level of C3a or a derivative thereof in a sample material of said patient can be determined by the above described detection techniques.

The following figures and example are given for illustrative purposes only. The invention is not to be construed to be limited to the following examples.

FIGURES

FIG. 1 shows the C3 protein sequence.

FIG. 2 shows (A) the C3a protein sequence and (B) the C3a-desArg protein sequence.

Figures 6, 6A:
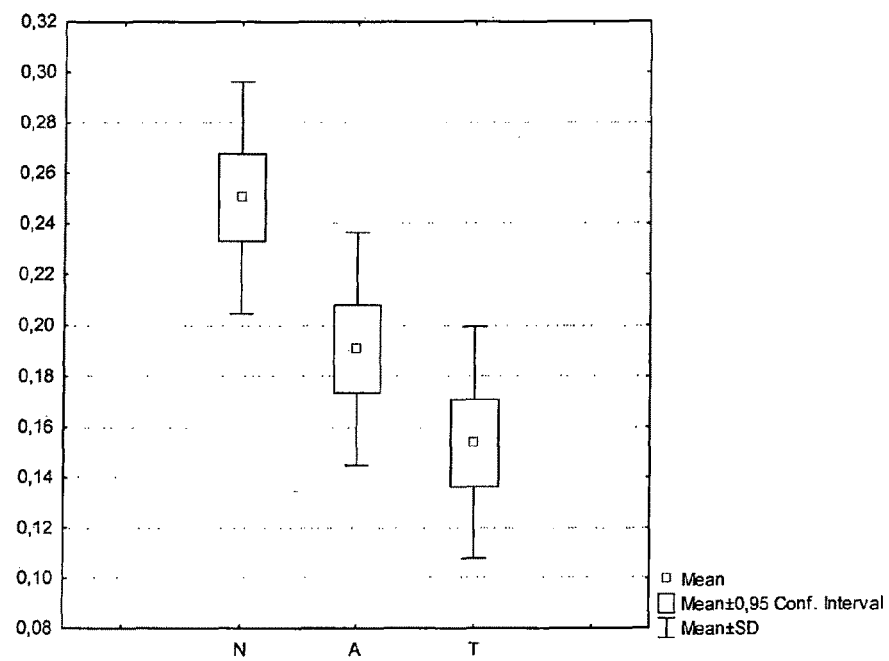

FIG. 6 shows the quantification of transthyretin by A) radial immunodiffusion and B) SELDI-TOF MS analysis. The mean transthyretin concentrations are significantly lower in the adenoma and cancer group compared to the non-cancerous control group. Further, the mean transthyretin concentrations are significantly lower in the cancer group compared with the adenoma group as measured by radial immunodiffusion. (A=adenoma group, N=healthy control group, T=cancer group)

Figure 7:
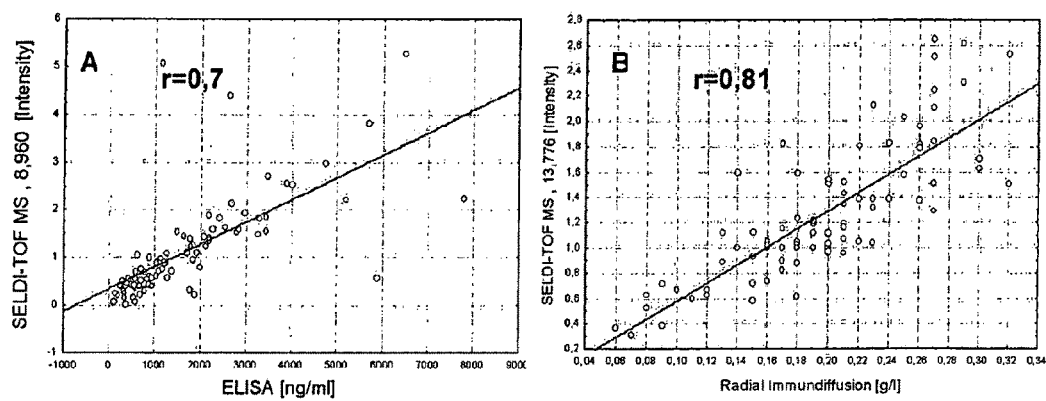

FIG. 7 shows the correlation between SELDI-TOF MS and immunoassay data. C3a-desArg (A) was analyzed by ELISA, transthyretin (B) by radial immunodiffusion.

EXAMPLES

Unless otherwise stated all methods were carried out following the protocol of the manufacturer of the analytical systems.

Serum Collection and Serum Fractionation

Serum from three groups of human patients were collected and investigated.

Group 1 consisted of 28 patients which were surgical patients treated for non-cancerous diseases such as inguinal hernia, gall bladder stones or diverticulitis. These individuals of group 1 were taken as the group of healthy individuals, i.e. those, who did not suffer from colorectal adenoma and/or colorectal carcinoma.

Group 2 consisted of 28 patients, who were all surgical patients treated for undefined tumors, which turned out to be benign colorectal adenoma.

Group 3 consisted of 28 patients, who were patients having colorectal carcinoma. All these 28 patients suffered from TNM stage III (Tumor, Node, Metastasis stage III) colorectal carcinoma.

Ethical guidelines and patient confidentiality have been strictly assured and all patients gave written consent to participate in this study. All patients had comparable preoperative preparations such as fasting time and medication at time of surgery.

Figure 3:
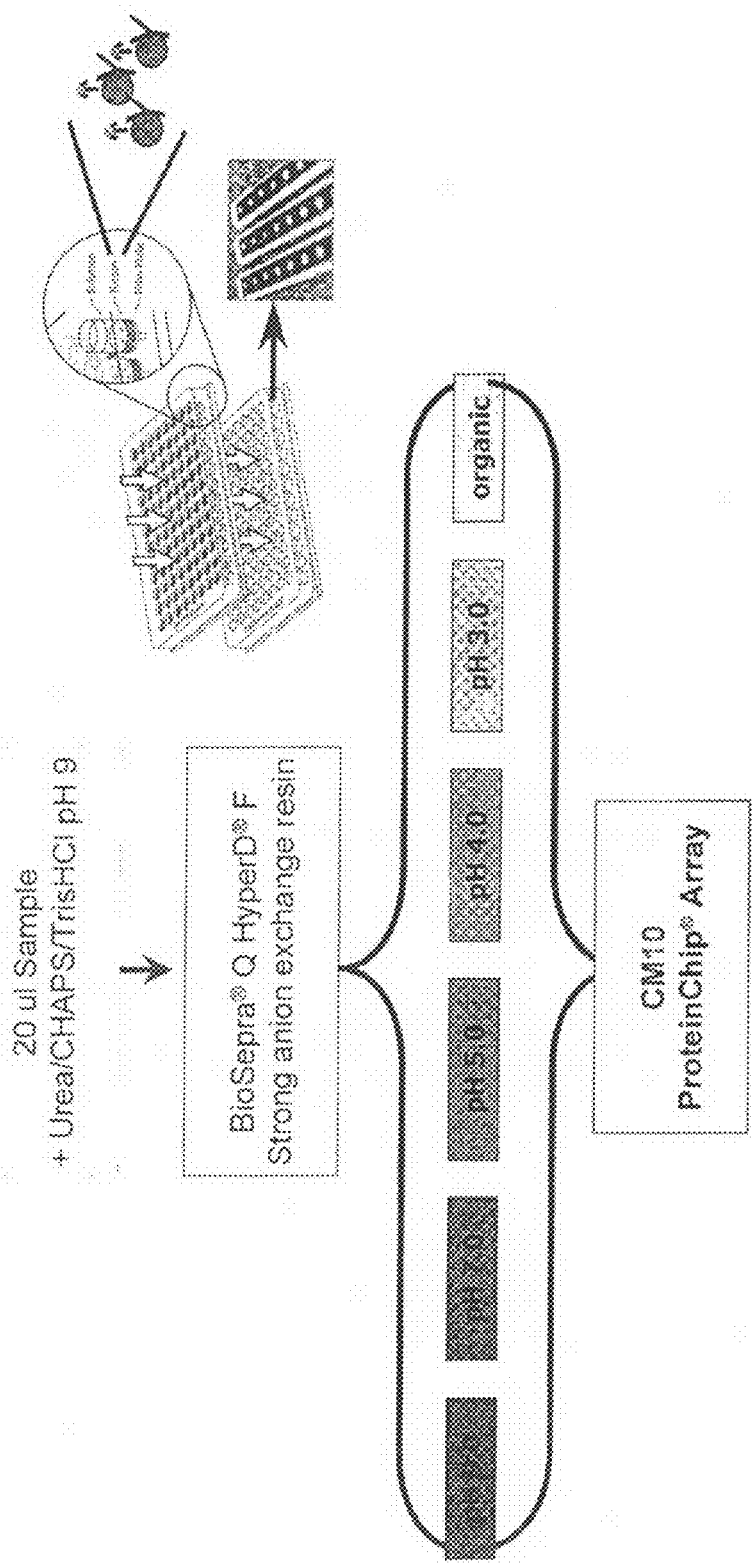
FIG. 3 shows a schematic diagram for fractionating and profiling of serum samples.

Serum from each patient was fractionated by anion exchange chromatography (Serum Fractionation Kit/Q HyperD resin, Ciphergen Biosystems, Inc.) using a 96 well format automation approach (Biomek2000, Ciphergen), according to the protocol of the manufacturer, to reduce some of the interference by the most abundant proteins. As shown in FIG. 3, the fractionation produced 6 fractions containing proteins separated roughly on the basis of the protein pI-value.

The C3A-desArg protein (p8,960 Da) was eluted with fraction 1 at pH 9.0 wash solution (50 mM Tris-HCl with 0.1% OGP (Octyl-β-D-glucopyranoside, pH 9.0) (according to the conditions defined by Ciphergen Biosystems Inc. expression difference mapping kit-serum fractionation cat. no K100-0007). The transthyretin protein (p 13,776 Da was eluted with fraction 4 at pH 4.0 (100 mM Sodium acetate with 0.1% OGP, pH 4.0 conditions (according to the conditions defined by Ciphergen Biosystems Inc. expression difference mapping kit-serum fractionation cat. no K100-0007).

SELDI-TOF-MS Analysis

CM10 protein arrays were processed in a bioprocessor (Ciphergen Biosystems, Inc.) according to the protocol of the manufacturer. Chips were equilibrated with CM10 binding buffer (Ciphergen Biosystems, Inc.) for 2×5 minutes and were subsequently incubated with the serum fractions (which had been diluted 1:10 in CM10 binding buffer). After 45 minutes the unbound material was removed and the chips were washed 3 times with CM10 binding buffer and 2 times with water. After drying at room temperature for 10 minutes, 2 applications of 0.05 M sinapinic acid (1.0 µl) were added and the chips were analyzed with the Ciphergen Protein ChipReader (model PBSII).

The Protein ChipReader is a time-of-flight mass spectrometer. The mass values and signal intensities for the detected proteins are transferred to a software, which is supplied by Ciphergen for further in-depth analysis by the ProteinChip Data Analysis Program and Biomarker Wizard Program.

To minimize data variability, measurement was performed within two days using samples from all patient groups randomly distributed on the chips. As a standard control for normalization, pooled normal serum was used parallel to all measurements.

The mass spectra of proteins were generated by using an average of 195 laser shots at a laser intensity of 185. The detector was run at a sensitivity of 7. For data acquisition, the detection size range was set between 2,000 and 40,000 Da. The laser was focused at 10,000 Da. The data were analyzed with the ProteinChip Data Analysis Program (version 3.1, Ciphergen Biosystems) and with the Biomarker Wizard Program (version 3.1, Ciphergen Biosystems). The peak intensities were normalized to the total ion current. It should be noted that the measured molecular weights may vary from measurement to measurement and may be dependent on the specifics of the used mass spectroscope. The measured molecular weight of C3desArg may be within the range of 8,950±25 Da.

C3a ELISA Analysis

For the quantitation of the C3a-desArg fragment in serum an enzyme immunoassay from Quidel was used (Quidel Corporation, 10165 McKellar Court, San Diego, Calif. 92121, USA). The ELISA was performed according to the manufacturer's instructions.

The microtiter strips included in the kit are coated with a monoclonal antibody (included in the immunoassay from Quidel) specific for human C3a-desArg. Samples were diluted 1:500 and incubated for one hour at 18-25° C. During this incubation, C3a-desArg in the specimen will bind to the monoclonal antibody. After rinsing off the unbound native C3, peroxidase-conjugated rabbit anti-C3a was used for the detection of bound C3a-desArg. Excess conjugate is removed through a washing step, and the amount of C3a-desArg in the serum sample was quantified using the peroxidase reaction and a standard curve.

Radial Immunodiffusion for the Quantification of Transthyretin

The radial immunodiffusion assay (Tina-Quant Prealbumin assay, Immunoturbidometric assay for the determination of prealbumin, Roche diagnostics GmbH, Mannheim, Germany, Cat.-No. 11660519) was performed in an clinical service laboratory. Serum was applied to a cylindrical well cut in a gel matrix containing a uniform concentration of monospecific antibodies. Antigen placed in the well diffuses radially, producing a precipitin ring. Precipitin rings can be read any time after overnight incubation, or endpoint. Results were quantitated by comparing the diameter of the precipitin ring produced by the sample to the precipitin rings produced by standards of known concentrations.

Statistical Evaluation of the Data

For the three patient groups cut-off values are calculated by the C&RT(CART) algorithmus on the basis of decision-tree analysis (Breiman, L., Friedman, J. H., Olshen, R. A., & Stone, C. J. (1984). *Classification and regression trees*. Monterey, C A: Wadsworth & Brooks/Cole Advanced Books & Software). The Cutoff-values have been calculated in order to select and specify the limiting values between the different analysis groups. The evaluation has been performed with STATISTICA Software Vs 7.1 from STATSOFT INC, the decision-tree analysis is performed with Data-Miner Modul subprogramm Standard Classification Trees (CAndRT) (StatSoft, Inc. (2005). STATISTICA (data analysis software system), version 7.1. www.statsoft.com.)

The statistical data are evaluated on the basis on the mean value and standard deviation. Further, the Figures show a confidence interval of mean±95, indicating to find the true mean values of prospect patient groups with 95% probability within this interval. The statistical evaluation is performed by the T-Test. The tests were considered as significant at p values $p<0.05$. The whiskers of the box plots show the standard deviation.

Example 1

In this experiment, the expression of C3a-desArg between serum from non-carcinoma patients (Group 1, n=28 patients) and serum from patients with colorectal adenoma (Group 2, n=28 patients) and colorectal carcinoma (Group 3, n=28 patients) were identified in duplicate by ELISA (Quidel C3a Enzyme immuno assay) and by SELDI-TOF MS analysis as described above.

Example 2

The expression of transthyretin was quantified by Radial immunodiffusion and by SELDI-TOF MS analysis as described above with the same patient collective.

Results and Statistical Evaluation

Figure 4:
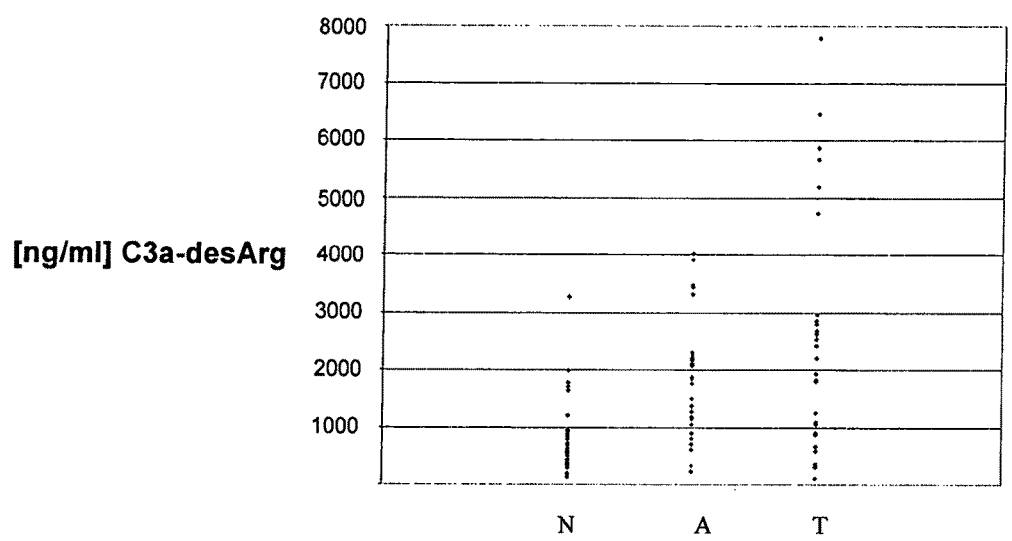
FIG. 4 shows the quantification of C3a-desArg using an ELISA. Serum samples from non-cancer (n=28), adenoma (n=28) and colorectal cancer patients (n=28) were assayed in duplicate in the Quidel C3a Enzyme Immunoassay. (A=adenoma group, N=healthy control group, T=cancer group)

As shown in FIG. 4, the intensity of the concentration of C3a-desArg [ng/ml] differs significantly between the three groups. The C3a-desArg level increases from healthy individuals over colorectal adenoma patients to colorectal carcinoma patients.

Table 1 shows the distribution of serum levels of C3a-desArg [ng/ml], and transthyretin [g/l] among 84 serum samples using SELDI-TOF MS and immunoassays (C3a-desArg-ELISA, transthyretin immunodiffusion) for validation. 28 serum samples in each group were measured.

TABLE 1

| Variable | Method | Mean ± Std. Dev. N | Mean ± Std. Dev. A | Mean ± Std. Dev. T | Mean ± Std. Dev. A + T | p-Value N vs. A | p-Value N vs. T | p-Value N vs. A + T | p-Value A vs. T |
|---|---|---|---|---|---|---|---|---|---|
| Transthyretin | Immunodiffusion | 0.250 ± 0.043 | 0.191 ± 0.035 | 0.154 ± 0.056 | 0.172 ± 0.05 | 0.000001 | 0.000001 | 0.000001 | 0.0046 |
| Transthyretin MG 13,776 Da | SELDI | 1.728 ± 0.462 | 1.123 ± 0.287 | 0.996 ± 0.497 | 1.060 ± 0.407 | 0.000001 | 0.000001 | 0.000001 | 0.247 |
| C3A-desArg | ELISA | 863.51 ± 678.93 | 1871.12 ± 1090.62 | 2513.33 ± 2060.46 | 2192.23 ± 1665.25 | 0.00011 | 0.000179 | 0.000117 | 0.150 |
| C3a-desArg MG 8,960 Da | SELDI | 0.5724 ± 0.387 | 1.363 ± 1.012 | 1.552 ± 1.271 | 1.458 ± 1.143 | 0.00030 | 0.000268 | 0.00015 | 0.541 |

Figures 5, 5A:
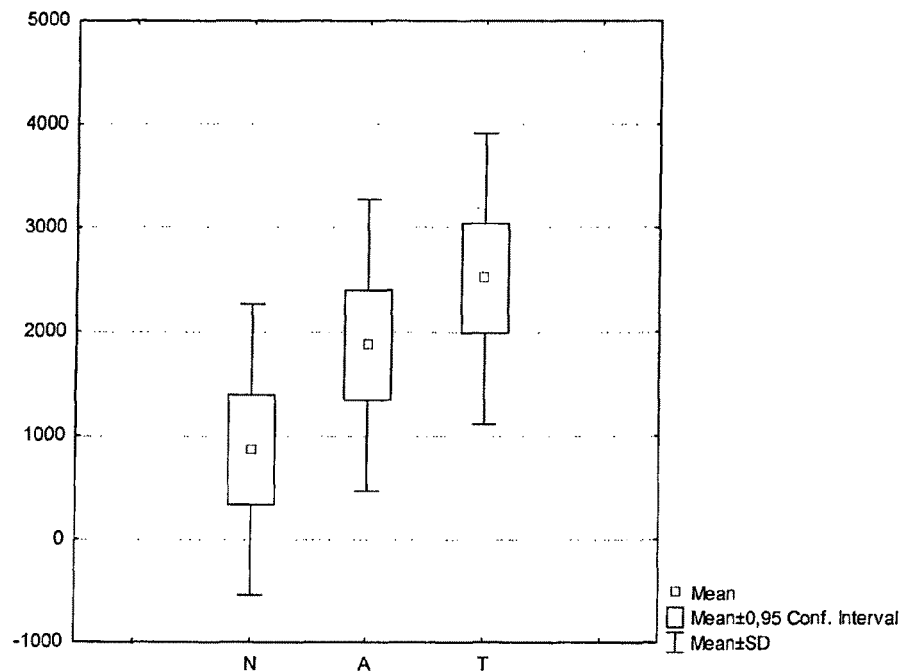
FIG. 5 shows the analysis of C3a-desArg by A) ELISA and B) SELDI-TOF MS. The mean C3a-desArg concentrations are significantly higher in the adenoma and cancer group compared to the non-cancerous control group. (A=adenoma group, N=healthy control group, T=cancer group)
Figure 5B:
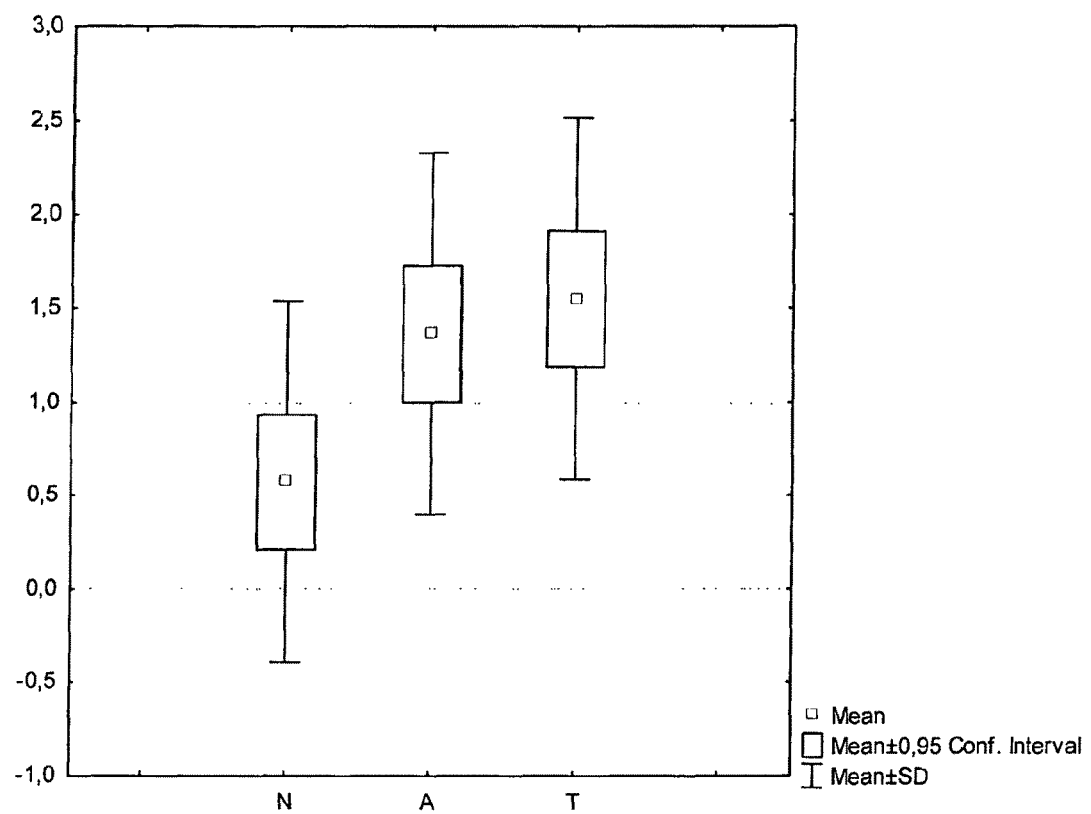

Serum concentrations of C3a-desArg measured by ELISA were significantly higher in adenoma and carcinoma patients compared to the non-cancerous control group (FIG. 5A). According to these data, a discrimination of healthy individuals from the cancer patients was possible. Furthermore, a discrimination between the healthy individuals and the adenoma patients was also possible. The results were very similar to the data achieved by SELDI-TOF MS analysis (FIG. 5B). In FIG. 7 the scatter plot of both methods (SELDI-TOF MS and ELISA) is shown, demonstrating a good correlation (FIG. 7A; r=0.7) between the intensity of p8,960 measured by SELDI-TOF MS and the concentration of C3a-desArg measured by ELISA of each patient as well as a good correlation (FIG. 7B, r=0.81) between the intensity of p13,776 measured by SELDI-TOF MS and the concentration of transthyretin measured by ELISA of each patient. This indicates that the results are independent from the analysis method.

Figure 6B:
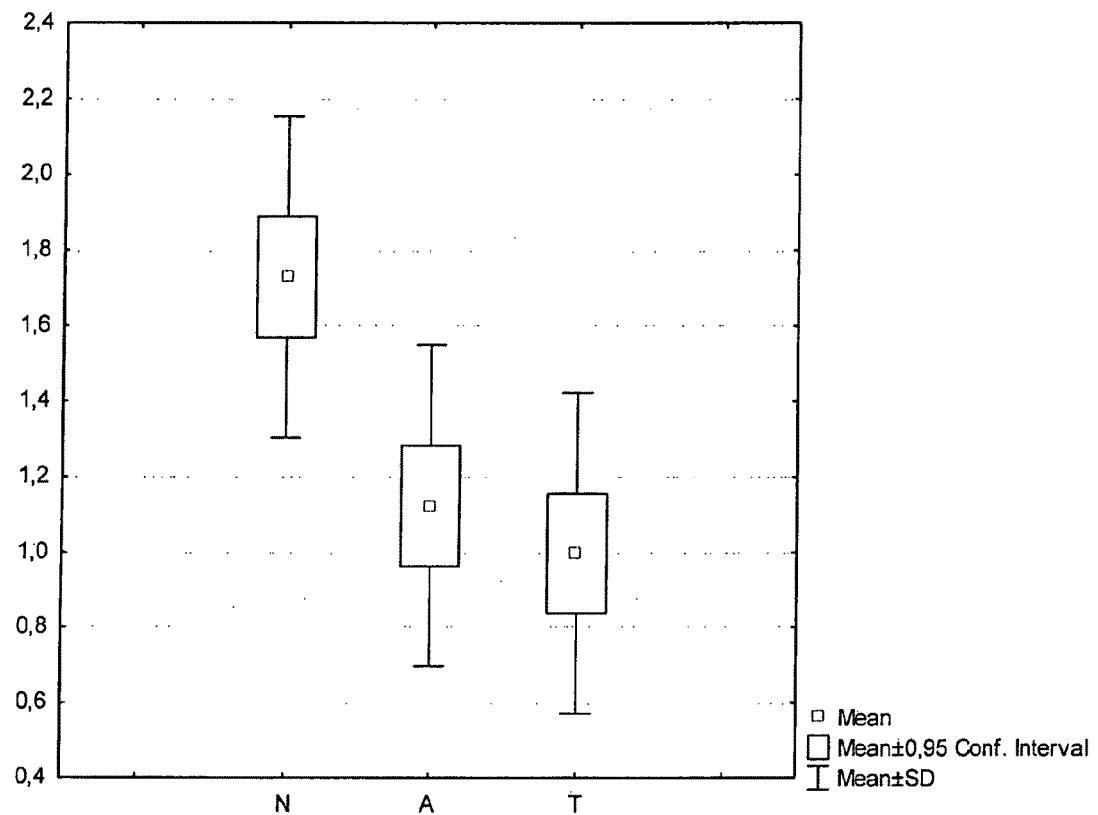

Transthyretin-data were generated by SELDI-TOF MS analysis (FIG. 6B) and were confirmed by radial immunodiffusion (FIG. 6A). Among patients with colorectal cancer transthyretin was significantly lower compared to non-cancer patients. Moreover, the transthyretin concentrations in serum of adenoma patients is still significantly lower than in normal serum.

Table 2 shows the comparison of sensitivity and specificity of C3a-desArg, measured by SELDI-TOF MS and ELISA, respectively, for the discrimination between healthy controls and adenoma/tumor patients.

TABLE 2

C3a-desArg (healthy controls versus Adenoma + Tumor patients)

| | ELISA |
|---|---|
| Sensitivity | 75% |
| Specificity | 78% |

Table 3 shows the comparison of sensitivity and specificity of transthyretin, measured by SELDI-TOF MS and radial immunodiffusion, respectively, for the discrimination between healthy controls and adenoma/tumor patients.

TABLE 3

Transthyretin (healthy controls versus Adenoma + Tumor patients)

| | SELDI-TOF MS | Radial Imunodiffusion |
|---|---|---|
| Sensitivity | 75% | 88% |
| Specificity | 90% | 70% |

Table 4 shows the comparison of sensitivity and specificity of both biomarkers (C3a-desArg/transthyretin) in combination. C3a-desArg and transthyretin were measured by immunoasay for the discriminiation between healthy controls and Adenoma/Tumor patients. Cutoff values for transthyretin (TTR) and C3a-desArg are shown in brackets.

TABLE 4

Combination of C3a-desArg and transthyretin (healthy controls versus Adenoma + Tumor patients)

| | SELDI-TOF MS | Radial Immunodiffusion/ELISA (TTR <0.22 and C3a-desArg >1000) |
|---|---|---|
| Sensitivity | 70% | 67% |
| Specificity | 100% | 89% |

Table 5 shows the sensitivity and specificity of C3a-desArg as single biomarker. C3a-desArg levels were measured by ELISA for the discrimination between healthy controls and adenoma and/or tumor patients. The cutoff values are shown in brackets.

TABLE 5

C3a-desArg

| | Normal vs. Adenoma | Normal vs. Tumor | Normal vs. Adenoma + Tumor |
|---|---|---|---|
| Sensitivity | 79% (</>990) | 61% (</>1786) | 75% (</>990) |
| Specificity | 78% | 93% | 78% |

Table 6 shows the sensitivity and specificity of transthyretin as single biomarker. Transthyretin levels were measured by radial immunodiffusion for the discrimination between healthy controls and adenoma and/or tumor patients. The cutoff values are shown in brackets.

TABLE 6

| | Transthyretin | | |
|---|---|---|---|
| | Normal vs. Adenoma | Normal vs. Tumor | Normal vs. Adenoma + Tumor |
| Sensitivity | 86% (</>0.225) | 61% (</>0.165) | 88% (</>0.22) |
| Specificity | 68% | 100% | 70% |

Table 7 shows the sensitivity and specificity of C3a-desArg and transthyretin (TTR) in combination. Transthyretin and C3a-desArg levels were measured by ELISA and radial immunodiffusion, respectively. The cutoff values are shown in brackets.

TABLE 7

| Combination of Transthyretin (TTR) and C3a-desArg | |
|---|---|
| | Normal vs. Adenoma |
| Sensitivity | 97% (</>0.225 TTR) and (</>1974 C3a-desArg) |
| Specificity | 70% |

These data show that C3a, optionally in combination with transthyretin, is(are) an excellent biomarker(s) for the detection of colorectal adenoma and/or colorectal carcinoma. In contrast to already known biomarkers CEA and CA 19-9 it is possible to discriminate between healthy individuals and adenoma patients. The sensitivity and specificity of the C3a test is high and allows an early specific detection of adenomas without a colonoscopy. In particular, the combination of the biomarkers C3a and transthyretin allows the detection of adenomas with an excellent sensitivity and high specificity.

The invention claimed is:

1. A method for detecting colorectal adenoma comprising:
   a) providing an isolated sample which has been taken from an individual,
   b) determining the level of C3a-desArg (SEQ ID NO:3) in said isolated sample, and
   c) comparing the determined level of C3a-desArg with one or more reference values, and wherein the level of C3a-desArg in a sample taken from a colorectal adenoma patient is higher compared to a sample taken from a healthy individual.

2. The method of claim 1, wherein in step (b) one or more additional biomarker(s) for detecting colorectal adenoma is/are determined in said isolated sample and wherein in step (c) the determined level of said additional biomarker(s) is/are compared with one or more respective reference values.

3. The method of claim 1, wherein said at least one additional biomarker(s) for detecting colorectal adenoma is selected from the group consisting of transthyretin, p53, CEA, CA 19-9, CA 15-3, CA-125, Kras, β-Catenin, Her-2/neu, C-reactive protein plasma and mutations in E-cadherin, MSH2, MSH3, MLH1, PMS1, PMS2, MSI-16 genes and
   microsatellite instability of MHL1 or MSH2 and SNPs and combinations thereof.

4. The method of claim 2, wherein the reference value(s) of C3a-desArg and the reference value(s) of the additional biomarker(s) and/or derivative(s) thereof is/are calculated as the average level of C3a-desArg and further biomarker(s) and/or derivative(S) thereof in a plurality of isolated samples of a respective group of individuals, wherein the group of individuals are healthy individuals, and/or colorectal adenoma patients.

5. The method of claim 2, wherein the reference value is/are individual reference value(s) calculated as the average level of C3a-desArg and said additional biomarker(s) and/or derivative(s) thereof determined in a plurality of isolated samples taken from said individual over a period of time.

6. The method of claim 1, wherein the isolated sample is a body fluid and is selected from the group consisting of blood, blood plasma, serum, bone marrow, stool, synovial fluid, lymphatic fluid, cerebrospinal fluid, sputum, urine, mother's milk, sperm, exudates and mixtures thereof.

7. The method of claim 2, wherein the level of said additional biomarker(s) in said sample material is determined by measuring DNA, mRNA and/or protein levels.

8. The method of clam 7, wherein the level of said additional biomarker(s) in said sample material is(are) determined by a nucleic acid hybridization technique, immunological methods or proteomics techniques, and/or mass spectroscopy.

9. The method of claim 1, wherein said method is carried out in combination with other diagnostic methods for colorectal adenoma.

10. A method for detecting colorectal adenoma comprising:
    a) providing a sample which has been taken from an individual; and
    b) determining the level of C3a-desArg (SEQ ID NO:3) in said sample, and wherein the level of C3a-desArg in a sample taken from a colorectal adenoma patient is higher compared to a sample taken from a healthy individual.

11. The method of claim 10, and further comprising determining the presence of one or more biomarkers, other than C3a-desArg for colorectal adenoma.

12. The method of claim 11, wherein said one or more biomarkers is selected from the group consisting of transthyretin, p53, CEA, CA 19-9, CA 15-3, CA-125, Kras, β-Catenin, Her-2/neu, C-reactive protein plasma, mutations in E-cadherin, MSH2, MSH3, MLH1, PMS1, PMS2, or MSH6 genes, microsatellite instability of MHL1 or MSH2, SNPs, and combinations thereof.

* * * * *